US011443867B2

(12) United States Patent
Ergler et al.

(10) Patent No.: US 11,443,867 B2
(45) Date of Patent: Sep. 13, 2022

(54) METHOD FOR PRODUCING A SCATTERED BEAM COLLIMATOR, SCATTERED BEAM COLLIMATOR AND X-RAY DEVICE WITH SCATTERED BEAM COLLIMATOR

(71) Applicant: Siemens Healthcare GmbH, Erlangen (DE)

(72) Inventors: Thorsten Ergler, Erlangen (DE); Stefan Wirth, Erlangen (DE); Vojislav Krstic, Erlangen (DE); Maria Magdalena Kolesnik-Gray, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 108 days.

(21) Appl. No.: 16/897,439

(22) Filed: Jun. 10, 2020

(65) Prior Publication Data

US 2020/0402682 A1    Dec. 24, 2020

(30) Foreign Application Priority Data

Jun. 19, 2019   (DE) .......................... 102019208888.0

(51) Int. Cl.
    *G21K 1/02*   (2006.01)
    *G21K 1/10*   (2006.01)
    (Continued)

(52) U.S. Cl.
    CPC ............... *G21K 1/02* (2013.01); *A61B 6/483* (2013.01); *G03F 7/2039* (2013.01); *G21K 1/10* (2013.01);
    (Continued)

(58) Field of Classification Search
    CPC ...... G21K 1/02; G21K 1/10; G21K 2207/005; G21K 1/025; A61B 6/483; A61B 6/032;
    (Continued)

(56) References Cited

U.S. PATENT DOCUMENTS 6,298,113 B1   10/2001  Duclos et al.
2008/0088059 A1*  4/2008  Tang ...................... G21K 1/025
                                                      264/261
(Continued)

FOREIGN PATENT DOCUMENTS

DE             10105239 A1    9/2001

OTHER PUBLICATIONS

Vink, T. J. et al. "Stress, strain, and microstructure in thin tungsten films deposited by dc magnetron sputtering", Journal of Applied Physics, 1993, vol. 74, pp. 988-995, https://doi.org/10.1063/1.354842.

*Primary Examiner* — Courtney D Thomas
(74) *Attorney, Agent, or Firm* — Harness, Dickey & Pierce, P.L.C.

(57) ABSTRACT

A method is for producing a scattered beam collimator starting from a lower side and extending in a build-up direction as far as an upper side, and having a large number of X-ray absorbing partitions, and in which pass-through channels for unscattered X-ray radiation are embodied between the partitions. A lithographic process is used, by which the partitions of the scattered beam collimator are formed from a photoresist into which an X-ray absorbing material is mixed.

19 Claims, 4 Drawing Sheets

(51) Int. Cl.
  *A61B 6/00*  (2006.01)
  *G03F 7/20*  (2006.01)
  *A61B 6/03*  (2006.01)
(52) U.S. Cl.
  CPC ........ *A61B 6/032* (2013.01); *G21K 2207/005* (2013.01)
(58) Field of Classification Search
  CPC ... A61B 6/4291; G03F 7/2039; G03F 7/0005; G03F 7/038; G03F 7/325; G03F 7/20
  See application file for complete search history.

(56) References Cited

U.S. PATENT DOCUMENTS

2015/0270413 A1    9/2015  Zhang et al.
2019/0384171 A1*  12/2019  Zi .......................... G03F 7/0042

* cited by examiner

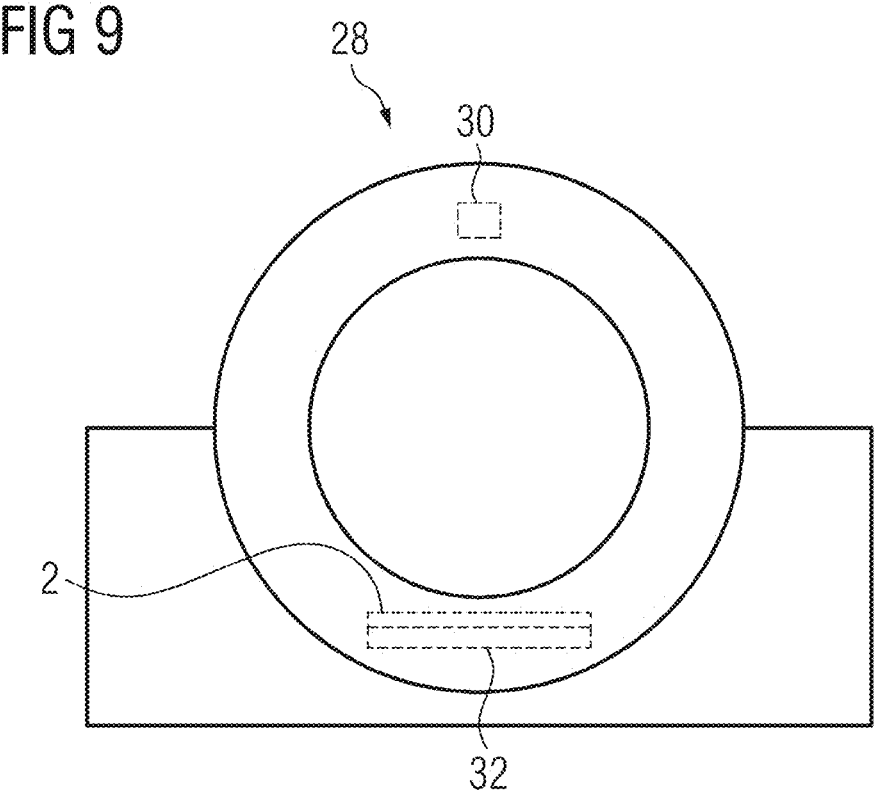

METHOD FOR PRODUCING A SCATTERED BEAM COLLIMATOR, SCATTERED BEAM COLLIMATOR AND X-RAY DEVICE WITH SCATTERED BEAM COLLIMATOR

PRIORITY STATEMENT

The present application hereby claims priority under 35 U.S.C. § 119 to German patent application number DE 102019208888.0 filed Jun. 19, 2019, the entire contents of which are hereby incorporated herein by reference.

FIELD

At least one embodiment of the invention generally relates to a method for producing a scattered beam collimator starting from a lower side and extending in a build-up direction as far as an upper side, and having a large number of X-ray absorbing partitions, and in which pass-through channels for unscattered X-ray radiation are embodied between the partitions. At least one embodiment of the invention generally relates to a corresponding scattered beam collimator and an X-ray device having a corresponding scattered beam collimator.

BACKGROUND

X-ray devices designed for an imaging method typically have what is known as a scattered beam collimator, also referred to as an anti-scatter grid, for absorbing undesired scattered X-ray radiation so that it does not strike the X-ray radiation detector of the X-ray device.

Here, a corresponding scattered beam collimator has a large number of X-ray absorbing partitions, between which pass-through channels for unscattered X-ray radiation are embodied. Scattered beam collimators of this type are generally produced by stacking metal sheets with suitable cut-outs or apertures one on top of another and then connecting them together.

SUMMARY

Embodiments of the invention disclose an advantageous method for producing a scattered beam collimator, an advantageously designed scattered beam collimator and an advantageously designed X-ray device.

The related claims contain in part advantageous and in part per se inventive developments of embodiments of this invention. The advantages listed in relation to the method and preferred embodiments can also be applied analogously to the scattered beam collimator and/or the X-ray device and vice versa.

The method according to at least one embodiment of the invention is used in this case for producing a scattered beam collimator or anti-scatter grid which, starting from a lower side, extends in a build-up direction as far as an upper side. Here, the scattered beam collimator has a large number of X-ray absorbing partitions, and pass-through channels for unscattered X-ray radiation are embodied between these partitions. Depending on the embodiment variant, here the pass-through channels are elongated and aligned parallel to one another, for example, or their central longitudinal axes all converge on a single point, for example, in particular on a point outside the scattered beam collimator.

At least one embodiment of the invention is directed to a method for producing a scattered beam collimator starting from a relatively lower side of the scattered beam collimator and extending in a build-up direction as far as a relatively upper side of the scattered beam collimator, the scattered beam collimator including a number of X-ray absorbing partitions, pass-through channels for unscattered X-ray radiation being embodied between the partitions, the method comprising:

forming the number of X-ray absorbing partitions of the scattered beam collimator, using a lithographic process, from a photoresist into which an X-ray absorbing material is mixed.

At least one embodiment of the invention is directed to a scattered beam collimator starting from the relatively lower side and extending in a build-up direction as far as the relatively upper side, and including the large number of X-ray absorbing partitions in which pass-through channels for unscattered X-ray radiation are embodied between the partitions, produced by the method of an embodiment.

At least one embodiment of the invention is directed to an X-ray device, comprising:
an X-ray radiation source;
an X-ray detector; and
the scattered beam collimator, arranged between the X-ray radiation source and the X-ray detector, of an embodiment.

BRIEF DESCRIPTION OF THE DRAWINGS

Example embodiments of the invention are explained in greater detail below on the basis of a schematic drawing, in which:

FIG. 9 shows a type of block circuit diagram of an X-ray device with a scattered beam collimator.

Parts corresponding to one another are labeled with the same reference characters in all the figures.

DETAILED DESCRIPTION OF THE EXAMPLE EMBODIMENTS

Figure 1:
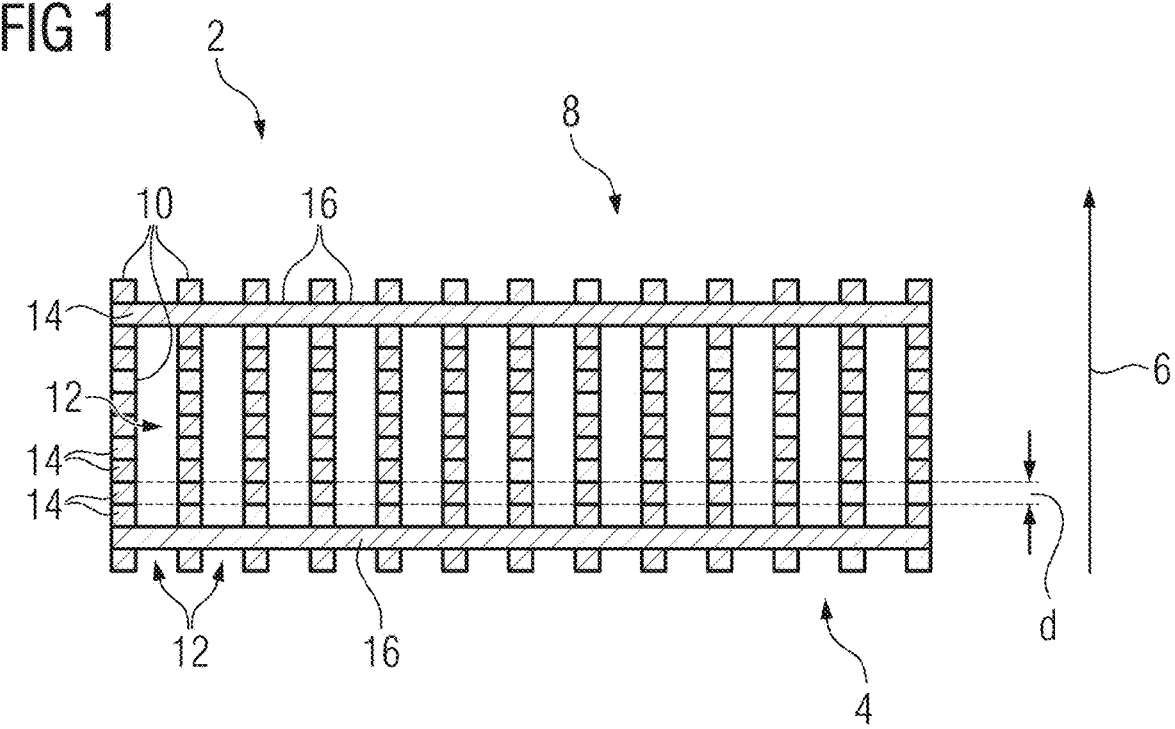
FIG. 1 shows a sectional representation of a first embodiment of the scattered beam collimator made of multiple layers.
Figure 2:
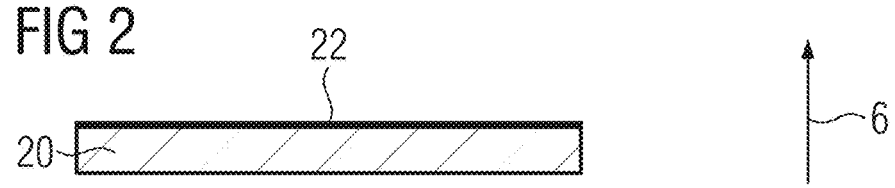
FIG. 2 shows a sectional representation of a substrate with a supporting layer deposited on it.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects.

Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The method according to at least one embodiment of the invention is used in this case for producing a scattered beam collimator or anti-scatter grid which, starting from a lower side, extends in a build-up direction as far as an upper side. Here, the scattered beam collimator has a large number of X-ray absorbing partitions, and pass-through channels for unscattered X-ray radiation are embodied between these partitions. Depending on the embodiment variant, here the pass-through channels are elongated and aligned parallel to one another, for example, or their central longitudinal axes all converge on a single point, for example, in particular on a point outside the scattered beam collimator.

Independently of this, the scattered beam collimator is produced by using a lithographic process and in particular by using this lithographic process repeatedly. In this case, an exposure mask is typically used in the course of the lithographic process and, by means of the lithographic process, the partitions of the scattered beam collimator are formed, specifically from a photoresist into which an X-ray absorbing material is mixed.

In this way, even very fine structures may be realized with very great precision. In this process, for example, X-ray absorbing partitions with a low partition thickness are realized, for example with a partition thickness in the range of approximately 10 µm to approximately 100 µm, and/or X-ray absorbing partitions in which the partition thickness hardly varies over their extension in the build-up direction. As an alternative or in addition, X-ray absorbing partitions are realized that are arranged at small distances relative to one another, for example with distances in the range of approximately 300 µm to approximately 600 µm.

Furthermore, in the course of the lithographic process a layer of the photoresist is typically exposed, generally to ultraviolet radiation. Following the exposure, the layer is developed and then, for example, inter alia in order to form pass-through channels, is rinsed or bathed in a solvent. I.e. such that parts of the layer of the photoresist are removed again with a solvent, and such that at least sections of pass-through channels are formed as a result of this removal. Gamma☐butyrolactone, for example, is considered to be a suitable solvent for this purpose.

Depending on the application case, a corresponding layer of the photoresist has a thickness here with a value in the range of approximately 200 µm to approximately 800 µm. In this context the thickness preferably lies in the range of approximately 400 µm to approximately 600 µm, for example approximately 500 µm.

According to one embodiment variant of the method, the photoresist has an epoxy resin as the base resin. In such a case, a Lewis acid is further preferably then used as a photosensitive component, for example triarylsulfonium hexafluoroantimonate. In particular, a photoresist from Microchem Corp. called SU-8 is considered to be appropriate.

Irrespective of the photoresist used and its precise composition, an X-ray absorbing material is mixed into the photoresist. Here, it is appropriate if a metal is used as the material, with tungsten being preferred.

In this process, the X-ray absorbing material is mixed into the photoresist in the form of a powder, for example, but preferably in the form of pellets or in the form of a granulate. If pellets or a granulate is/are provided, the pellets or the granules of the granulate preferably have an average diameter in the range of approximately 1 µm to approximately 10 µm.

Moreover it is advantageous if the volumetric proportion of the X-ray absorbing material in the mixture of photoresist and X-ray absorbing material makes up at least approximately 30% and in particular at least approximately 40%, i.e. approximately 50% for example. Furthermore, the volumetric proportion of the X-ray absorbing material typically has a value of less than approximately 80% and in particular less than approximately 70%.

Such a mixture of photoresist and X-ray absorbing material is now preferably used to form the partitions of the scattered beam collimator. To this end, it is appropriate if a substrate is used, for example a silicon wafer, and the scattered beam collimator or a module of the scattered beam collimator is preferably then built up in layers on this substrate in the build-up direction, in particular by repeating the lithographic process multiple times.

In the course of each lithographic process, typically a layer of photoresist and X-ray absorbing material is applied, wherein it is appropriate if the first layer is applied to the substrate and wherein the further layers are then generally applied one after another to the previously completed layers. Here, the application is preferably performed by means of spin coating. Alternatively, the application of each layer is performed by the substrate being surrounded with a type of frame and the mixture of photoresist and X-ray absorbing material then being poured in.

When building up the layers, depending on the intended application, different exposure masks are used for different layers or one exposure mask is used for all layers. By using different exposure masks, webs may be formed in individual layers between the X-ray absorbing partitions, for example, which hold the X-ray absorbing partitions together and thereby also fix them to one another in their relative positions and relative orientations. As an alternative or in addition, with the aid of different exposure masks, pass-through channels may be formed that are not aligned parallel to one another and are in particular not parallel to the build-up direction, the central longitudinal axes of which pass-through channels then converge on a single common point, for example.

In certain cases, a coating process is also performed between two lithographic processes in order to form a stabilizing intermediate layer, and after each lithographic process a coating process of this type is preferably then performed. Preferably, a coating process of the type mentioned is typically omitted only after the final lithographic process.

A stabilizing intermediate layer of this type is, for example, a metallic coating, i.e. a coating of tungsten, for example. In particular, if the stabilizing intermediate layer is formed by a metallic coating, the stabilizing intermediate layer is preferably formed by means of sputtering. Alternatively, the stabilizing intermediate layer is deposited by means of dip-coating. A dip-coating layer of this type is then advantageous especially in cases where a special paint is applied in order to form the stabilizing intermediate layer. In certain cases, the intermediate layer has a honeycomb-type structure. A honeycomb-type structure of this kind is then typically also generated by means of optical lithography.

Irrespective of the manner in which the stabilizing intermediate layer is deposited and which material is used for this purpose, after its formation the stabilizing intermediate layer preferably has a thickness with a value in the range between approximately 10 μm and approximately 50 μm.

Depending on the application case, parts of the previously described stabilizing intermediate layer are removed again after they have been deposited, for example by means of etching. In these cases, it is appropriate if parts are removed that do not cover the structures formed of the photoresist, in other words the formed sections of the partitions, but rather those positioned in the vicinity of the pass-through channels to be formed.

Furthermore it is appropriate if, between two lithographic processes, free spaces between the structures formed of the photoresist are filled with a filling material, and in particular are completely filled. Here, a material is generally used as the filling material that does not react sensitively to the exposure, and in particular therefore does not react sensitively to ultraviolet light (UV light). A suitable material is polymethylmethacrylate (PMMA). Depending on the intended application, the filling material is removed again at a later point in time, for example after the final lithographic process. Common solvents may be used for this purpose, such as acetone.

By way of at least one embodiment of the method described above, an inventive scattered beam collimator is now produced, which is designed in particular for an imaging X-ray apparatus, in other words an X-ray device, and is generally also used in an X-ray device, for example a computed tomography apparatus. A scattered beam collimator of this type typically has an extension in the build-up direction of between approximately 5 mm and approximately 30 mm. When the scattered beam collimator is used in an X-ray device, this build-up direction is then generally aligned substantially parallel to a line through the X-ray radiation source of the X-ray device, which line falls perpendicular to the X-ray radiation detector of the X-ray device.

The extension of the scattered beam collimator at right angles to the build-up direction varies depending on the intended application. In this context, the scattered beam collimator typically has a substantially rectangular cross-section at right angles to the build-up direction. Here, typically one side length of the rectangular cross-section is approximately 2 cm to approximately 4 cm, and typically the other side length is approximately 12 cm.

In certain cases, the scattered beam collimator is designed as a single piece or single part. Alternatively, the scattered beam collimator is built up of modules, which are typically designed to be substantially identical and, viewed at right angles to the build-up direction, are arranged next to one another in the scattered beam collimator. In this context, a quantity of modules generally lies in the range 2 to 8.

A scattered beam collimator 2 described below by way of example is reproduced schematically in FIG. 1 and, starting from a lower side 4, extends in a build-up direction 6 as far as an upper side 8. Here, the scattered beam collimator 2 has a large number of X-ray absorbing partitions 10, between which pass-through channels 12 for unscattered X-ray radiation are embodied.

In the example embodiment, all pass-through channels 12 have central longitudinal axes that are not shown, which are aligned parallel to the build-up direction 6. Alternatively, a different geometry, for example a conical geometry, is realized. In the case of such an alternative embodiment variant, the central longitudinal axes of the pass-through channels 12 all converge on a single point, wherein when the scattered beam collimator 2 is used, an X-ray radiation source 30 is then typically set in this point.

It has already been indicated in FIG. 1 that the scattered beam collimator 2 is built up in layers, i.e. layers 14, wherein in the example embodiment all layers 14 have approximately the same thickness. Here, the layer thickness d is typically approximately 500 μm. It is also apparent from FIG. 1 that webs 16 are formed between the partitions 10 in the example embodiment, which webs connect the partitions 10 to one another and consequently in effect hold the scattered beam collimator 2 together.

As an alternative or in addition, the pass-through channels 12 are filled and in particular completely filled with a filling material 18 not shown in FIG. 1, wherein it is then appropriate if such a filling material 18 is substantially transparent to X-ray radiation. Irrespective of whether the scattered beam collimator 2 has webs 16 and/or whether the pass-through channels 12 are filled or completely filled with a filling material 18, in certain embodiment variants the scattered beam collimator 2 has an enclosure or a type of housing (not shown), which is then designed in particular to hold the partitions 10 in their positions relative to one another. A housing of this type (not shown) is then also typically produced from a material that is permeable to X-ray radiation.

As already indicated, according to an embodiment of the invention the scattered beam collimator 2 is built up in layers 14. Here, each layer 14 is produced by means of a lithographic process, which will be explained in greater detail below with the aid of the representations in FIG. 2 to FIG. 6.

First, a substrate 20, for example a substrate 20 made of silicon or silicon dioxide, is generally prepared for the production of the scattered beam collimator 2. For this purpose, the substrate 20 is cleaned with piranha acid (piranha clean), for example.

Furthermore, a base layer or supporting layer 22 is firstly then preferably also applied to or deposited on the substrate 20, wherein after the scattered beam collimator 2 has been completed or at least after the partitions 10 have been completed, this supporting layer 22 facilitates removal or separation of the scattered beam collimator 2 from the substrate 20. Typically a (complex) polymer, for example cyclopentanone, is used for the production of such a supporting layer 22. A suitable solvent may then be used for the removal, for example tetramethylammonium hydroxide (TMAH).

Figure 3:
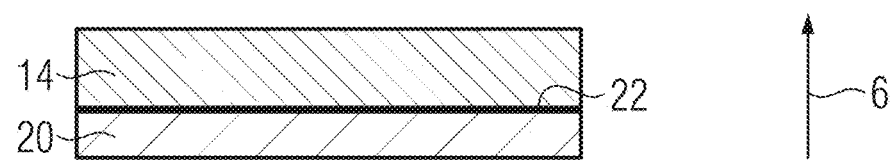
FIG. 3 shows a sectional representation of the substrate with the supporting layer and also with a first unfinished layer of the first embodiment of the scattered beam collimator deposited on it.

In a subsequent process step, a first layer 14 is applied for the formation of the partitions 10. In this context, the layer 14 consists of a photoresist into which, in the example embodiment, tungsten pellets have been mixed as an X-ray absorbing material. Here, the application is preferably performed by means of spin coating. In this way, a layer 14 is applied with a layer thickness d corresponding to approximately 500 µm. The result is shown in FIG. 3.

Alternatively, the application of the layer 14 is performed by the substrate 20 being surrounded with a type of frame and the mixture of photoresist and tungsten pellets then being poured in.

Figure 4:
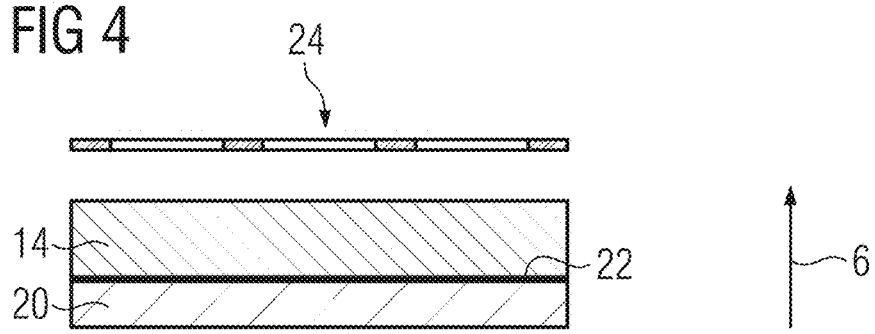
FIG. 4 shows a sectional representation of the substrate with the supporting layer and the first unfinished layer of the first embodiment of the scattered beam collimator, together with an exposure mask.

Later, using an exposure mask 24, the applied layer 14 is irradiated with ultraviolet light. This is indicated in FIG. 4.

Figure 5:
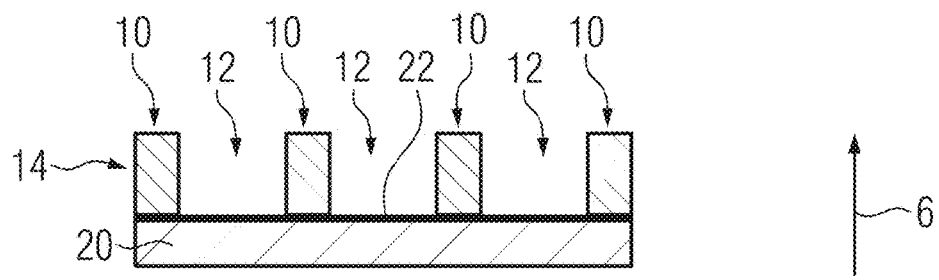
FIG. 5 shows a sectional representation of the substrate with the supporting layer and the finished first layer of the first embodiment of the scattered beam collimator after a development process.
Figure 6:
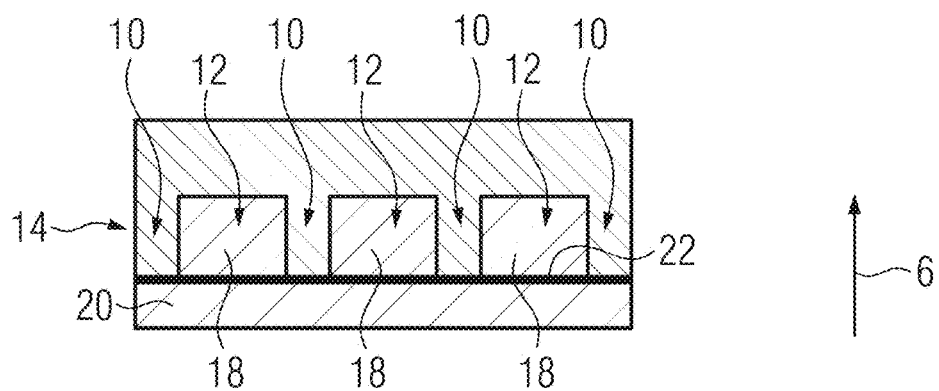
FIG. 6 shows a sectional representation of the substrate with the supporting layer, with the finished first layer of the first embodiment of the scattered beam collimator, and also with an unfinished second layer.

The photoresist is then developed, wherein the development includes at least one curing process and one rinse with a solvent, depending on the photoresist. The result is shown in FIG. 5. It is apparent from this that the layer 14 is structured, wherein the structural elements represent parts of partitions 10, i.e. in particular one layer 14 of the partitions 10. The intermediate spaces then embody in particular a layer 14 of the pass-through channels 12.

In order to complete the first layer 14, the intermediate spaces between the structural elements made of the photoresist with mixed-in tungsten pellets are filled with the aforementioned filling material 18. After that, the next layer 14 of photoresist with mixed-in tungsten pellets is then applied and the lithographic process is repeated.

In this way, the scattered beam collimator 2 is built up in layers or at least the partitions 10 are built up in layers. Depending on the embodiment variant, the exposure masks used in this process for each layer 14 are different, or the same exposure mask is used for multiple layers 14.

Figure 7:
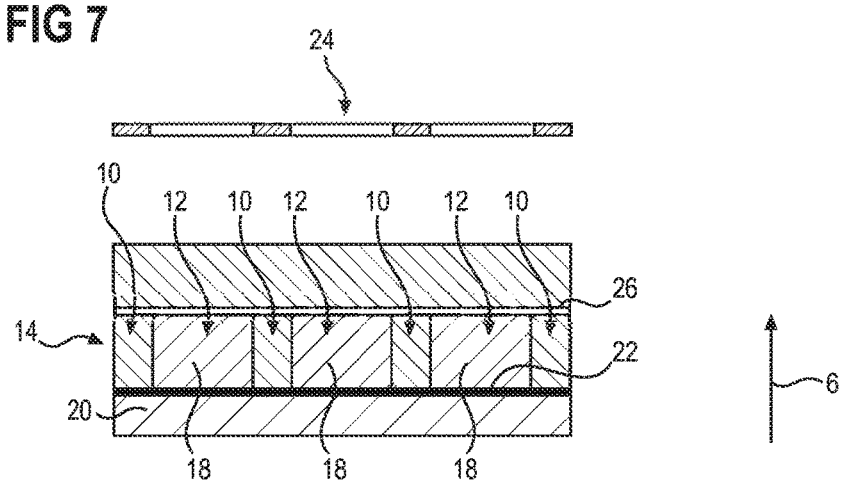
FIG. 7 shows a sectional representation of a substrate with a supporting layer, with a finished first layer of a second embodiment of the scattered beam collimator, with an unfinished second layer, and also with an intermediate layer.

According to an alternative embodiment variant, each lithographic process includes an additional coating process that is performed either before or after the intermediate spaces have been filled with the filling material 18. Here, a stabilizing intermediate layer 26 is then applied, for example by means of sputtering, which is approximately 50 µm thick, for example, and depending on the embodiment variant is made of tungsten, for example. An intermediate layer 26 of this type is shown in FIG. 7.

Figure 8:
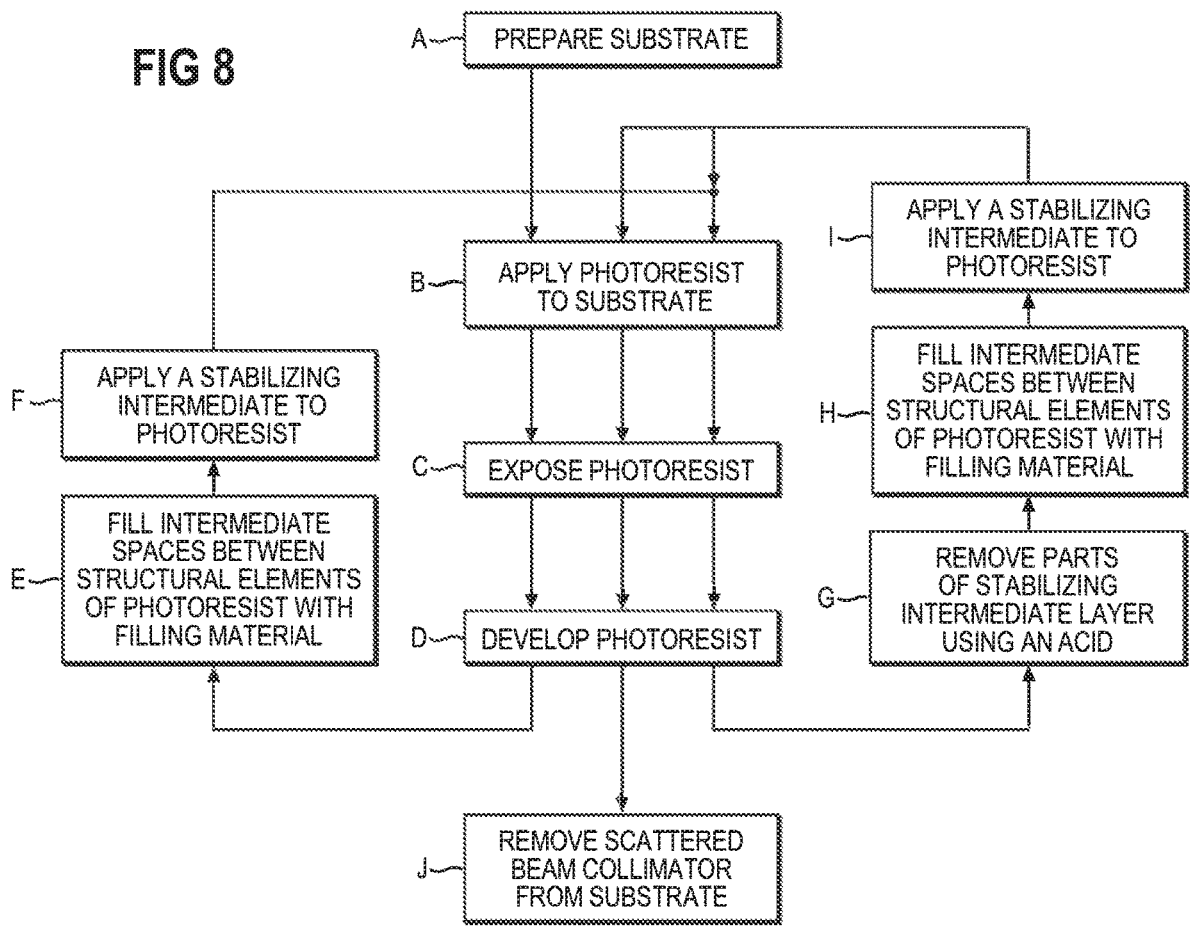
FIG. 8 shows a block diagram of a method for producing a scattered beam collimator.

The production of a further embodiment variant of the scattered beam collimator 2 is reproduced in a block diagram in FIG. 8. Here, once again the substrate 20 is first prepared in a method step A, i.e. typically cleaned and, for example, coated with the supporting layer 22.

A layer 14 of photoresist is then applied in a method step B. Using the exposure mask 24, this layer is exposed in a method step C and finally developed in a method step D.

When the method steps B to D have been completed for the first time, the method steps E and F then follow, wherein in the method step E the intermediate spaces between the structural elements formed of the photoresist are filled with the filling material 18 and wherein in the method step F a stabilizing intermediate layer 26 is applied over the whole surface.

The method steps B to D once again then follow the method steps E and F, followed by three method steps G to I. In the method step G, parts of the previously deposited stabilizing intermediate layer 26 are removed again using an acid. Here, the parts are removed that do not cover the structures formed of the photoresist, in other words the formed sections of the partitions, but rather those positioned in the vicinity of the pass-through channels to be formed. Conversely, the parts that cover the structures formed of the photoresist are protected by the overlying structures made of photoresist, in other words the overlying layer 14 of partitions 10 made of photoresist. In the method step H, the intermediate spaces provided between the structural elements formed of the photoresist are filled with the filling material 18 and in the method step F a stabilizing intermediate layer 26 is applied over the whole surface.

After that, the method steps B, C, D, G, H and I are repeated until the intended penultimate layer 14 of the scattered beam collimator 2 has been formed. This is followed by the method steps B to D being performed once again, and the method is finally completed with a method step J in which finishing is carried out, for example removal of the scattered beam collimator 2 from the substrate 20.

Irrespective of its precise embodiment, a previously described scattered beam collimator 2 is preferably fitted and used in an X-ray device 28 as indicated in FIG. 9. Said X-ray device is designed, for example, as a computed tomography apparatus and has the aforementioned X-ray radiation source 30 and an X-ray detector 32. The scattered beam collimator 2 is then arranged between the X-ray radiation source 30 and the X-ray detector 32.

The invention is not limited to the example embodiment described above. Rather, other variants of the invention can also be derived herefrom by the person skilled in the art, without departing from the subject matter of the invention. In particular all the individual features described in relation to the example embodiment can also be combined differently with one another, without departing from the subject matter of the invention.

Although the invention has been illustrated and described in greater detail with reference to the referred example embodiments, the invention is not restricted thereby. Other variations and combinations can be derived herefrom by the person skilled in the art without departing from the essential concept of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for producing a scattered beam collimator starting from a lower side of the scattered beam collimator and extending in a build-up direction to an upper side of the scattered beam collimator, the scattered beam collimator including a number of X-ray absorbing partitions with pass-through channels for unscattered X-ray radiation embodied between the X-ray absorbing partitions, the method comprising:
   forming the number of X-ray absorbing partitions of the scattered beam collimator, using a lithographic process, from a photoresist into which an X-ray absorbing material is mixed; wherein
      the X-ray absorbing material is mixed into the photoresist such that a volumetric proportion of the X-ray absorbing material is at least approximately 30%.

2. The method of claim 1, further comprising:
   exposing a layer of the photoresist in a course of the lithographic process, and
   following the layer of the photoresist being exposed, at least one of rinsing or bathing the layer in a solvent to form the pass-through channels.

3. The method of claim 2, wherein a layer of the photoresist has a thickness with a value in a range of 200 μm to 800 μm.

4. The method of claim 1, wherein the photoresist has an epoxy resin as a base resin.

5. The method of claim 1, wherein the X-ray absorbing material includes a metal.

6. The method of claim 1, wherein X-ray absorbing material is mixed into the photoresist in a form of pellets.

7. The method of claim 1, wherein a substrate is used.

8. The method of 7, further comprising:
   building up the scattered beam collimator or a module of the scattered beam collimator in layers on the substrate, in a build-up direction, by repeating the lithographic process.

9. The method of claim 8, further comprising:
   forming a stabilizing intermediate layer by performing a coating process between two lithographic processes.

10. The method of claim 9, wherein the forming a stabilizing intermedia layer comprises:
    forming a metallic coating as the stabilizing intermediate layer via the coating process, by sputtering.

11. The method of claim 9, wherein the stabilizing intermediate layer has a thickness between 10 μm and 50 μm.

12. The method of claim 8, further comprising:
    filling, with a filling material, free spaces between structures formed of the photoresist between two lithographic processes.

13. A scattered beam collimator starting from the lower side and extending in a build-up direction to the upper side, the scattered beam collimator including the number of X-ray absorbing partitions in which pass-through channels for unscattered X-ray radiation are embodied between the X-ray absorbing partitions, the scattered beam collimator produced by the method of claim 1.

14. The scattered beam collimator of claim 13, wherein the build-up direction extends between 5 mm and 30 mm.

15. An X-ray device, comprising:
    an X-ray radiation source;
    an X-ray detector; and
    the scattered beam collimator of claim 13, arranged between the X-ray radiation source and the X-ray detector.

16. The X-ray device of claim 15, wherein the X-ray device is embodied as a computed tomography apparatus.

17. The method of claim 2, further comprising:
    at least one of rinsing or bathing the layer in a gamma-butyrolactone solvent, to form the pass-through channels.

18. The method of claim 3, wherein a layer of the photoresist has a thickness in a range of 400 μm to 600 μm.

19. The method of claim 5, wherein the metal is tungsten.

* * * * *